United States Patent
Hefner, Jr. et al.

(10) Patent No.: US 9,487,615 B2
(45) Date of Patent: *Nov. 8, 2016

(54) POLYCYANATES OF CYCLODODECANE POLYPHENOLS AND THERMOSETS THEREOF

(71) Applicant: Dow Global Technologies LLC, Midland, MI (US)

(72) Inventors: Robert E. Hefner, Jr., Rosharon, TX (US); Erich J. Molitor, Midland, MI (US)

(73) Assignee: Dow Global Technologies, LLC

( * ) Notice: Subject to any disclaimer, the term of this patent is extended or adjusted under 35 U.S.C. 154(b) by 59 days.

This patent is subject to a terminal disclaimer.

(21) Appl. No.: 14/375,335

(22) PCT Filed: Feb. 22, 2013

(86) PCT No.: PCT/US2013/027246
§ 371 (c)(1),
(2) Date: Jul. 29, 2014

(87) PCT Pub. No.: WO2013/126643
PCT Pub. Date: Aug. 29, 2013

(65) Prior Publication Data
US 2014/0378627 A1    Dec. 25, 2014

Related U.S. Application Data

(60) Provisional application No. 61/602,890, filed on Feb. 24, 2012.

(51) Int. Cl.
| | | |
|---|---|---|
| *C08G 8/04* | (2006.01) | |
| *C08G 8/28* | (2006.01) | |
| *C07C 261/02* | (2006.01) | |
| *C08G 73/06* | (2006.01) | |

(52) U.S. Cl.
CPC .............. *C08G 8/28* (2013.01); *C07C 261/02* (2013.01); *C08G 8/04* (2013.01); *C08G 73/0655* (2013.01); *C07C 2101/20* (2013.01)

(58) Field of Classification Search
CPC ..... C07C 37/20; C07C 39/17; C07C 261/02; C07C 2101/14
See application file for complete search history.

(56) References Cited

U.S. PATENT DOCUMENTS

| | | |
|---|---|---|
| 2011/0009559 A1 | 1/2011 | Mullins et al. |
| 2011/0009562 A1 | 1/2011 | Mullins et al. |
| 2012/0238668 A1 | 9/2012 | Metral et al. |
| 2012/0238709 A1 | 9/2012 | Metral et al. |
| 2012/0289624 A1 | 11/2012 | Metral et al. |

FOREIGN PATENT DOCUMENTS

WO    2013/126641 A1    8/2013

OTHER PUBLICATIONS

Whittington, The term "cured" or "thermoset" as defined by L.R. Whittington, Whittington's Dictionary of Plastics, p. 239, 1968.
Martin, et al., Cyanic Acid Esters From Phenols: Phenyl Cyanate, Organic Synteses, vol. 612, p. 35, 1983.
Mathew, Bisphernol a Dicyanate-Novolac Epoxy Blend: Cure Characteristics, Physical and Mechanical Properties, and Applications in Composites, Journal of Applied Polymer Science, vol. 74, Issue 7, pp. 1675-1685, 1999.
Reams, et al. Effect of Chemical Structure and Network Formation on Physical Properties of Di(Cyanate Ester) Thermosets, ACS Applied Materials and Interfaces, vol. 4, Issue 2, pp. 527-535, 2012.

*Primary Examiner* — Shane Fang

(57) ABSTRACT

Polycyanates of the formula:

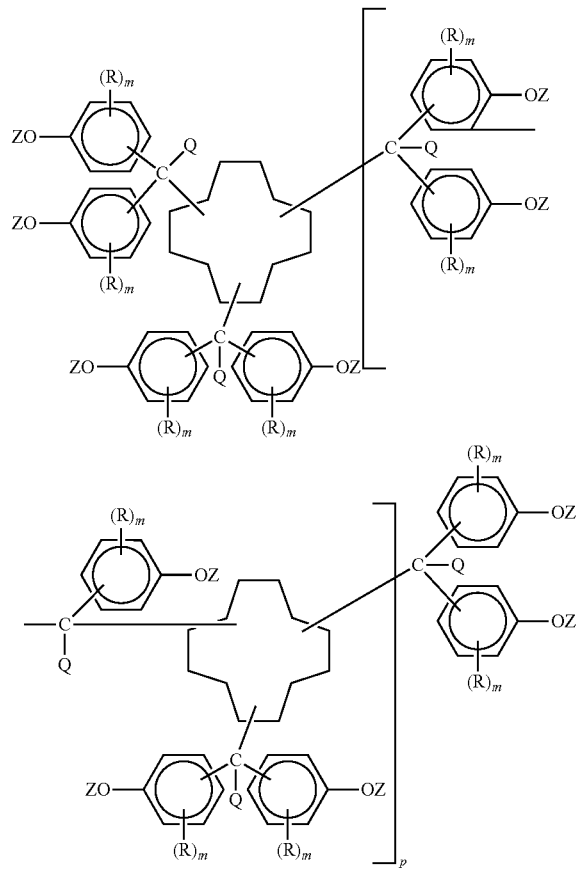

where R, m, Q, p and Z are as defined herein. Methods of curing said polycyanates and methods of using said polycyanates to provide high Tg thermoset products.

19 Claims, No Drawings

POLYCYANATES OF CYCLODODECANE POLYPHENOLS AND THERMOSETS THEREOF

CROSS REFERENCE TO RELATED APPLICATIONS

This application is a 35 USC §371 national phase filing of PCT/US2013/027246 filed Feb. 22, 2013, which claims the benefit of U.S. Application No. 61/602,890, filed Feb. 24, 2012.

FIELD OF THE INVENTION

Disclosed herein are methods of preparing and using cyanate resins based on the polyphenols of cyclododecane (hereinafter, "CDD"). The cyanate resins may be used to create new oligomers and/or thermoset polymers.

BACKGROUND OF THE INVENTION

Phenolic compounds and resins are synthetic materials that vary greatly in molecular structure. This variety allows for a multitude of applications for these compounds; for example, use as a curing agent and/or to prepare the corresponding epoxy, cyanate and/or allyl thermosettable monomers and resins. These curing agents and/or monomers can provide enhanced physical and/or mechanical properties to a cured composition, such as increased glass transition temperature (Tg). To achieve improved properties, however, would require the thermosettable monomer to have a high functionality (i.e., chemical groups available for cross linking). However, as the functionality increases in these monomers, so does their molecular weight, which increases the melt viscosity of the monomer and can lead to difficulties in using such monomers. Likewise high functionality in the thermosettable monomers can lead to excessive enthalpic cure energy. Excessive exothermicity on curing can damage parts, such as laminates, composites or castings, causing cracking or delamination.

One strategy for preparing thermosettable monomers is to convert a phenol, such as bisphenol A, into the corresponding cyanate. Bisphenol A dicyanate (cyanuric acid ester of 4,4'-isopropylidenediphenol) (BPA DCN) was the first dicyanate monomer offered commercially and still serves as an industry standard. While the homopolytriazine of BPA DCN provides a relatively high 275° C. Tg, numerous problems were encountered. These problems included incomplete curing, generation of excessive enthalpic cure energy, poor moisture resistance and brittleness leading to deficiency in certain mechanical properties, notably tensile elongation and fracture toughness. One attempted solution to the deficiencies employs BPA DCN as a reactive component in blends with other thermosettable monomers, notably epoxy resins and bis(maleimide)s. While the blends generally afford some improvement in processing and mechanical properties, Tg is also typically reduced. Furthermore, tradeoffs in mechanical property improvements exist. For example in cured blends of BPA DCN with a novolac epoxy resin, oxazolidinone structure from the co-polymerization can modestly enhance flexural strength, but at the expense of large (>50%) decreases in tensile strength [Mathew, et al., Journal of Applied Polymer Science, volume 74, pages 1675-1685 (1999)]. Another attempted solution, toughening with thermoplastic additives, required control over phase separation during the cyclotrimerization reaction to prevent deterioration of Tg. Recent publication by Reams, et al. (ACS online publications, ACS Applied Materials & Interfaces, Feb. 6, 2012, dx.doi.org/10.1021/am201413t) provides extensive investigation of complex moisture resistance problems associated with BPA DCN.

Another approach to improvement of thermoset cyanate resins uses a phenolic precursor with different chemical structure. One example is taught in published U.S. Patent Application Number 2011/0009559, where the diphenol, 1,1-bis(4-hydroxyphenyl)cyclododecane, is converted to the corresponding dicyanate. Homocyclotrimerization of this dicyanate gave a Tg of 202.1° C., which is a substantial reduction from the 275° C. Tg for homocyclotrimerized BPA DCN, but it also had enhanced thermal resistance, gave low moisture absorption, excellent dielectric properties and moderation of the enthalpic cure energy, without increasing the cure onset and end temperatures.

There is unmet need for a polycyanate capable of homocyclotrimerization to give a polytriazine with a Tg substantially higher than 300° C. Likewise there is a need for a polycyanate which can be blended with other cyanates such as BPA DCN and/or other thermosettable monomers such as bis(maleimide)s to produce copolytriazines or copolymers, respectively, with a Tg above 275° C. while improving curing profile (for example decrease onset to cure temperature and enthalpic cure energy).

Thermosets of cyanate resins of CDD polyphenols have now surprisingly been found to provide remarkable Tg's (>400° C.) and improved cure profile including rapid onset to cure and reduced cure enthalpy. Furthermore when used in blends with other thermosettable monomers, for example with BPA DCN or the bismaleimide of 4,4'-diaminodiphenylmethane, cyanate resins of CDD polyphenols may impart increased Tg, thermal stability and/or improved cure profile to the thermosets thereof. Improvements in one or more of these properties provide higher performance thermosets, useful in structural or electrical laminates and/or composites, multilayer electronic circuitry, integrated circuit packaging (such as "IC substrates"), filament windings, moldings, encapsulations, castings, composites for aerospace applications, adhesives, functional powder coatings and other protective coatings. The cured compositions described herein are particularly useful in the aerospace and electronics industries and may be used in the form of sheets, films, fibers or other shaped articles.

SUMMARY OF THE INVENTION

In related U.S. application No. 61/602,840, filed Feb. 24, 2012, Applicants reported the preparation of the trialdehyde of cyclododecatriene and its subsequent conversion to polyphenols such as the hexaphenol. Applicants now report the conversion of the CDD polyphenols to the corresponding thermosettable polycyanates. Said polycyanates may be blended with one or more other thermosettable monomers or resins, such as BPA DCN and optionally with one or more curing catalysts to form a curable blend having increased Tg, increased thermal stability and/or improved cure profile when compared to thermosets of BPA DCN alone. The high functionality of the polycyanates disclosed herein provide high crosslink density upon curing. This high crosslink density translates to very high Tgs, enhanced thermal stability, more rapid development of Tg during curing, and improved reactivity on curing, as demonstrated in the Examples (below).

In one aspect, disclosed herein are polycyanates of CDD polyphenols represented by Formula 1:

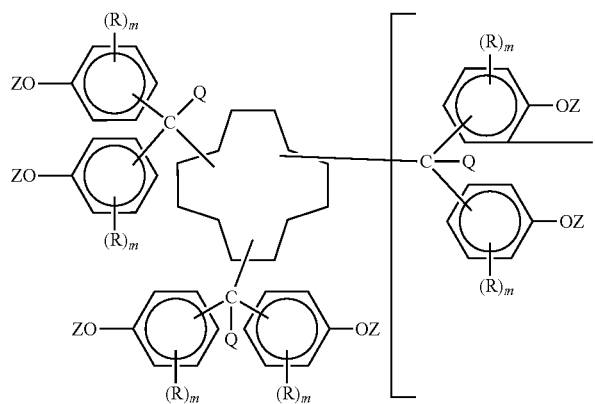
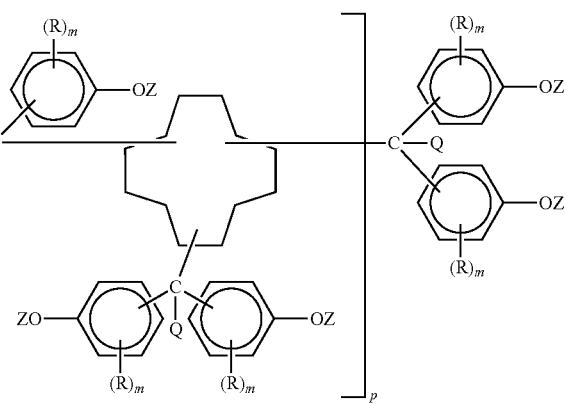

where each Z is an H or —C≡N group, wherein at least 25% of the Z groups are —C≡N; each m independently has a value of zero to 3, p has a value of zero to 20, preferably zero to 5, most preferably zero to 1; each R is independently halogen, preferably fluorine, chlorine or bromine; nitrile; nitro; $C_1$-$C_6$ alkyl or $C_1$-$C_6$ alkoxy preferably the alkyl and alkoxy groups independently have 1 to 4, most preferably 1 to 2 carbon atoms which may be substituted with one or more halogen atoms, preferably chlorine or bromine; or $C_2$-$C_6$ alkenyl or $C_2$-$C_6$ alkenyloxy, preferably the aforeappreciated that mixtures of compounds having the carbon bonded to the Q in both the ortho and the para position relative to the —OH group are possible. It is also possible to have the carbon bonded to Q in the meta position relative to the —OH group.

In another aspect, disclosed herein are methods of making the polycyanates of Formula 1, using polyphenols of Formula 2 as a starting material:

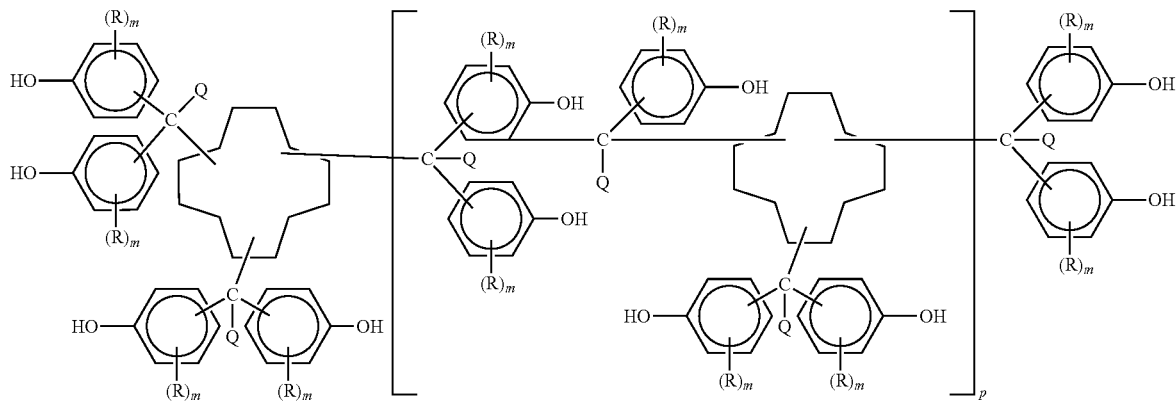

mentioned alkenyl groups have 2 to 4, most preferably 2 to 3 carbon atoms; and each Q is independently hydrogen or $C_1$-$C_6$ alkyl, preferably the alkyl group has 1 to 4, most preferably 1 to 2 carbon atoms; two R groups may independently be a $C_3$-$C_4$ alkylene group that optionally contains one or two double bonds and is bonded to two adjacent carbons on the ring to which it is attached; thereby producing a fused, bicyclic ring system, such as naphthyl, tetrahydronaphthyl, indenyl or indanyl.

It should be understood that the composition of the compounds of Formula 1 can be mixtures with various values of p. For such mixtures the values of p can be described as number average degrees of oligomerization. Likewise, it should be understood that the composition of the compounds of Formula 1 can be mixtures where a part of Z is —C≡N with the remaining part of Z being —H (unreacted —OH) as shown in the Examples (below).

For the various embodiments, when m has a value other than zero, the carbon bonded to Q is preferably in the ortho and/or para position relative to the —OH group. It is where R, Q, m and p are as hereinbefore defined.

In another aspect, disclosed herein are curable compositions, partially oligomerized or polymerized (B-staged) products, or cured (thermoset) products comprising 1) a cyanate resin of Formula 1, 2) optionally, one or more thermosettable monomers other than the cyanate of Formula 1, and, optionally, 3) at least one curing catalyst and/or curing accelerator.

DETAILED DESCRIPTION

As used herein, the term "thermoset" refers to a polymer that can solidify or "set" irreversibly when heated. The terms "curable," "cured," "thermosettable" and "thermoset" are synonyms and mean the composition is capable of being converted to a cured or thermoset state or condition. The term "cured" or "thermoset" is defined by L. R. Whittington in Whittington's Dictionary of Plastics (1968) on page 239 as follows: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

The term "B-stage" as used herein refers to a thermoset resin that has been thermally reacted beyond the A-stage so that the product has full to partial solubility in a solvent such as an alcohol or a ketone.

In one embodiment, preferred compounds of Formula 1 are compounds of Formula 3, i.e., compounds of Formula 1, where p is as previously defined, each m is 0; each Q is H; and at least 50% of the Z groups are —C≡N. More preferably, 80-100% of the Z groups are —C≡N. Compounds of Formula 3 wherein at least about 80% of the Z groups are —C≡N are especially useful in preparation of thermosets with very high Tg.

Mixtures of CDD diphenols and/or tetraphenols with hexaphenols plus oligomers, if any, may be employed to prepare the disclosed polycyanates. An example of the tetrapolycyanate with saturated CDD ring is represented by Formula 4:

preferred, and reaction temperatures of −10° C. to 0° C. being most preferred. Reaction times can vary substantially, for example, as a function of the reactants being employed, the reaction temperature, solvent(s) used, the scale of the reaction, and the like, but are generally between 15 minutes and 4 hours, with reaction times of 30 minutes to 90 minutes being preferred.

Suitable cyanogens halides include, but are not limited to, cyanogen chloride, cyanogen bromide and cyanogen iodide, with cyanogen chloride and bromide being more preferred. Alternately, the method of Martin and Bauer described in Organic Synthesis, vol. 61, pages 35-68 (1983) published by John Wiley and Sons can be used to generate the required cyanogen halide in situ from sodium cyanide and a halogen such as chlorine or bromine.

Suitable base compounds include both inorganic bases and tertiary amines such as sodium hydroxide, potassium hydroxide, trimethylamine, triethylamine, Hunig's base, mixtures thereof, and the like. Triethylamine is a preferred base compound. Suitable solvents for the cyanate-forming reaction can include water, aliphatic and cycloaliphatic ketones, chlorinated hydrocarbons, aliphatic and cycloaliphatic ethers and diethers, aromatic hydrocarbons, mixtures thereof and the like. Acetone, methylethylketone, methylene

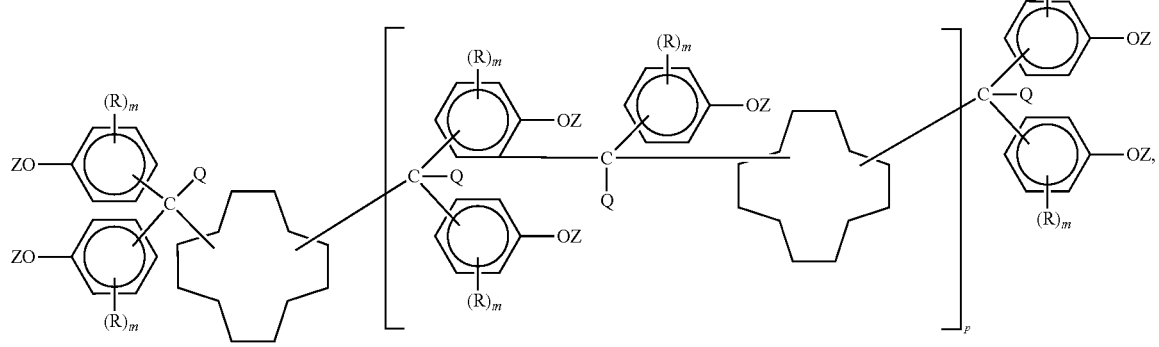

where Z, R, Q, m, and p are as hereinbefore defined. When p is 0, the tetracyanate free of oligomers is produced. When p is greater than 0, an oligomeric component is present. When only a part of Z is —C≡N, the remaining part of Z is —H (unreacted —OH).

A preferred method of making polycyanates of Formula 1 comprises reacting polyphenols of Formula 2 with a cyanogen halide using 0.5 to 1.25, more preferably 0.95 to 1.15, most preferably 1.0 to 1.05 equivalents of a cyanogen halide per equivalent of phenolic hydroxyl group in the presence of 0.5 to 1.25, more preferably 0.95 to 1.15, most preferably 1.0 to 1.05 equivalents of a base compound per phenolic hydroxyl group and in the presence of a suitable solvent. The reaction can also take place in the presence or absence of a catalyst. When less than stoichiometric cyanogen halide is used it follows that some portion of the Z groups will be —H (unreacted —OH). While polycyanates of Formula 1 having 25%-50% of the —OH groups represented by Z converted to —C≡N groups are preferred, polycyanates wherein 50%-80% of the Z groups are —C≡N are more preferred, while polycyanates wherein at least 80%-100% of the Z groups are —C≡N are most preferred.

Reaction temperatures of −40° C. to 60° C. are operable, with reaction temperatures of −15° C. to 10° C. being chloride or chloroform are particularly suitable as the solvent. The solvent may be substantially inert to the cyanate-forming reaction including inert to the reactants, the intermediate products if any, and the final products. The solvent may be removed at the completion of the cyanate-forming reaction using conventional means, such as, for example, vacuum distillation. Alternatively, all or a part of the solvent may also be left in the polycyanate product to provide a solvent borne polycyanate which may be used later, for example, in the preparation of coating or film.

Analytical methods, such as high pressure liquid chromatography (HPLC), may be employed to monitor reaction of the CDD polyphenols concurrently with the formation of the polycyanates of CDD polyphenols.

Recovery and purification of the polycyanates of CDD polyphenols can be performed using a variety of methods. For example, gravity filtration, vacuum filtration, centrifugation, water washing or extraction, solvent extraction, decantation, column chromatography, vacuum distillation, falling film distillation, and other processing methods and the like may be used. Vacuum distillation, such as rotary evaporation, is a preferred method for removal of lighter boiling fractions, such as solvent and residual base compound, if present, which may be recycled.

Oligomers present in the polycyanates may arise from (1) cyanate-forming reaction of oligomeric components present in the CDD polyphenols (Formula 2 where a part up to all of p is greater than 0) or from (2) partial in situ reaction of cyanate groups, for example to form the substituted triazine group.

Condensation reactions (phenolation) employing a large excess of the phenol and/or substituted phenol have been found to favor CDD polyphenol precursors to the polycanate having a low polydispersity and weight average molecular weight. Likewise, as the amount of the phenol and/or substituted phenol is reduced, there can be an increase in oligomers of the CDD polyphenols, increasing the weight average molecular weight. Increased oligomer content favors higher hydroxyl functionality per molecule which may be highly beneficial for certain end uses, for example, increasing the Tg, but at the cost of higher viscosity. Thus, while very large excesses of phenol and/or substituted phenol may be used, Reference Example 1 (below) employs a molar ratio needed to produce products rich in CDD polyphenol and low in oligomers.

Starting with the CDDT trialdehydes allows for a high level of functionality to be achieved in the resulting CDD polyphenols without a large increase in the compound's Mw. This is not the case with previous attempts to form polyphenols with high levels of functionality. For example, embodiments of the present disclosure provide for functionalities of about 6 at hydroxyl equivalent weights as low as about 120 grams per hydroxyl equivalent. Embodiments of the present disclosure may also allow for a scalable progression in the level of functionality to be achieved without significant increases in the molecular weight and viscosity of the curable composition.

The polycyanate compounds of Formula 1 achieve a high level functionality (i.e., greater than 2, more preferably greater than 3, still more preferably greater than 4, even more preferably 5 or more functional groups per molecule) with a relatively low molecular weight, which may allow for a relatively low melt viscosity of the curable composition. The polycyanates can have a polydispersity index (PDI, which is known in the art as a measure of distribution of molecular mass in a given polymer sample of less than 2. For example, the PDI of the polycyanates can be from 1.3 to 1.4. These types of results indicate that the p values for the polycyanates are very uniform. This result is surprising, as phenolation reactions used to form the precursor to the polycyanates (Formula 2) often times produce products having a much larger polydispersity (e.g., from 2 to 5). Having a uniform chain length for the polycyanates allows for more desirable viscosity predictability in the viscosity of the curable compositions of the present disclosure. The polydispersity values for certain of polycyanates of the present disclosure are indicative of an increase in the level of functionality without substantial increase in Mw. High functionality and the resultant high crosslink density can provide very desirable high Tg.

Also disclosed herein are curable compositions, partially oligomerized or polymerized (B-staged) products, or cured (thermoset) products comprising 1) a polycyanate resin of Formula 1, 2) optionally, one or more thermosettable monomers other than the cyanate of Formula 1, and, optionally, 3) at least one curing catalyst and/or curing accelerator. One or more thermosettable monomers, for example, di- and poly(cyanate)s other than the cyanate of Formula 1, bis- and poly(maleimide)s, epoxy resins, di- and poly(isocyanate)s, di and poly(cyanamide)s, polymerizable mono-, di-, or poly(ethylenically unsaturated) monomers, including acrylates and methacrylates, vinyl benzyl ethers, allyl and allyloxy compounds may also be included in the curable compositions. A catalytic amount of one or more curing catalysts (or co-catalysts) and/or curing accelerators can also be used with a curable composition of the present disclosure. Examples of suitable catalysts include, but are not limited to acids, bases, salts, nitrogen and phosphorus compounds such as for example, Lewis acids such as $AlCl_3$, $BF_3$, $FeCl_3$, $TiCl_4$, $ZnCl_2$, $SnCl_4$, boric acid, protonic acids such as HCl, $H_3PO_4$, aromatic hydroxyl compounds such as phenol, p-nitrophenol, nonylphenol, pyrocatechol, dihydroxynaphthalene, sodium hydroxide, sodium methylate, sodium phenolate, trimethylamine, triethylamine, tributylamine, diazabicyclo[2.2.2]octane, 1-methylimidazole, 2-methylimidazole, 2-phenylimidazole, quinoline, isoquinoline, tetrahydroisoquinoline, tetraethylammonium chloride, pyridine-N-oxide, tributylphosphine, triphenylphosphine, zinc octoate, tin octoate, zinc naphthenate, cobalt naphthenate, cobalt octoate, cobalt acetylacetonate and the like. Also suitable as catalysts are the metal chelates such as, for example, the chelates of transition metals and bidentate or tridentate ligands, particularly the chelates of iron, cobalt, zinc, copper manganese, zirconium, titanium, vanadium, aluminum and magnesium. Cobalt naphthenate, cobalt octoate, cobalt acetylacetonate, and manganese octoate are most preferred as the catalysts. Nonyl phenol is most preferred as a co-catalyst. Accelerating compounds such as DMP-30 (tris(1,3,5-dimethylaminomethylene) phenol), triethanolamine, and amine salts of carboxylic acids such as triethylammonium stearate can be used.

The curable compositions comprising the polycyanate of Formula 1 can be cured (thermoset) at atmospheric (e.g. 760 mm Hg), superatmospheric or subatmospheric pressures by heating from 50° C. to 400° C. preferably by heating from 100° C. to 300° C., optionally in the presence of a catalytic amount of one or more catalysts (or co-catalysts) and/or accelerators. Time required to complete the curing may depend upon the temperature employed. Higher temperatures generally require a shorter period of time whereas lower temperatures generally require longer periods of time. The quantity of catalyst and/or accelerator used, if any, depends on the structure of the particular catalyst, the structure of the polycyanate being cured, the structure of any additional thermosettable monomers used in the formulation, the cure temperature, the cure time, and the like. Generally, catalyst concentrations of from 0.001 to 2 percent by weight are preferred. The cured compositions prepared from the polycyanates of Formula 1 can possess the cyanate group homopolymerization structure, the polytriazine ring, unless other functionalities are present in the polycyanate that participate in the curing process.

It is also possible to partially cure (B-stage) the curable compositions and then complete the curing at a later time. B-staging or prepolymerization of the curable compositions can be accomplished by using lower temperatures and/or shorter curing times. Subsequent curing of the formed B-stage product can then be accomplished by increasing the temperature and/or curing time.

The curable compositions, partially oligomerized or polymerized (B-staged) products may also be formulated with other components such as but not limited to core/shell rubbers, thermoplastics including polyethersulfones, polysulfones, polyetherimides, polyesters, phenoxy resins, polyoelfins and polyurethanes. The resultant curable formulation may then be fully cured. Cured compositions of the present disclosure may also be combined with one or more other components such as those aforementioned.

The curable compositions of the present disclosure can be blended with other materials, such as solvents or diluents, fillers, pigments, dyes, flow modifiers, thickeners, reinforcing agents, mold release agents, wetting agents, stabilizers, fire retardant agents, surfactants, or combination thereof. Reinforcing agents which can be employed herein include natural and synthetic fibers in the form of woven fabric, mats, monofilament, multifilament, unidirectional fibers, rovings, random fibers or filaments, inorganic fibers or whiskers, hollow spheres, among others. Suitable reinforcing materials include, for example, glass, ceramics, nylon, rayon, cotton, aramid, graphite, silicon carbide, polybenzoxazoles, polyesters such as polyalkylene terephthalates, polyethylene, polypropylene, aluminum oxide, boron, combinations thereof, or hybrids thereof. Suitable fillers which can be employed herein include, for example, inorganic oxides, ceramic microspheres, plastic microspheres, or combinations thereof.

The amount of these other additives used with the curable compositions of the present disclosure can vary widely as a function of the polycyanate of the present disclosure used, the additional thermosettable monomers used in the formulation if any, the type of curing catalyst(s) and/or accelerator(s) used, the processing temperature(s) employed, the type of additive(s) used, the processing method(s) used, and other known variables.

The following examples are illustrative of the present invention, but are not to be construed as to limiting the scope thereof in any manner.

EXAMPLES

Reference Example 1

Synthesis of Polyphenol of Cyclododecane Trialdehyde

CDD trialdehyde obtained from the hydroformylation of cyclododecatriene was analyzed by gas chromatography demonstrating the following composition: cyclododecatriene (0.15 wt. %), CDD monoaldehyde (0.16 wt. %), CDD dialdehyde (9.52 wt. %) and CDD trialdehyde (88.72 wt. %). Reaction of CDD trialdehyde (39.74 g, 0.16 mole, 0.48 aldehyde eq) and molten phenol (301.2 g, 3.2 moles) using 3-mercapto-1-propane sulfonic acid catalyst (total catalyst used was 1.25 g, 0.05 mole % with respect to CDD trialdehyde reactant) provided the polyphenol of CDD trialdehyde as a reddish tan colored powder (107.00 g). HPLC analysis of a sample of the product demonstrated the presence of 1.89 area % residual phenol. FTIR spectrophotometric analysis of a KBr pellet revealed complete disappearance of the aldehyde carbonyl stretch at 1721.9 $cm^{-1}$ with appearance of strong aromatic ring absorbance at 1610.8 (shoulder at 1595.5) and 1510.2 $cm^{-1}$, broad strong hydroxyl O—H stretching centered at 3382.3 $cm^{-1}$, and broad strong C—O stretching at 1229.4 (shoulder at 1170.5) $cm^{-1}$. HPLC analysis revealed the polyphenol of CDD trialdehyde included multiple components eluting between 3.24 to 8.30 min (phenol residual eluted at 2.49 min).

Example 1

Synthesis of Polycyanate of the Polyphenol of Cyclododecane Trialdehyde (Containing Residual Unreacted Hydroxyl)

A 500 milliliter, three neck, glass, round bottom reactor was charged with 2.56 grams of polyphenol of cyclododecane trialdehyde (nominally 0.02 hydroxyl equivalent) from Reference Example 1, anhydrous dichloromethane (250 milliliters) and anhydrous acetone (75 milliliters). The reactor was additionally equipped with a condenser (maintained at 0° C.), a thermometer, an overhead nitrogen inlet (1 liter per minute used), a septum covered port, and magnetic stirring. Stirring commenced at to room temperature (22° C.) to provide a solution followed by placement of a dry ice-acetone bath for cooling under the reactor. The stirred solution was cooled to 8° C. then cyanogen bromide (2.23 grams, 0.02105 mole, 1.05:1 cyanogen bromide:nominal hydroxyl equivalent ratio) was added to the solution and dissolved therein. The solution was further cooled to −8° C. while being stirred. Triethylamine (2.06 grams, 0.0204 mole, 1.02 triethylamine:nominal hydroxyl equivalent ratio) in a polypropylene syringe was added to the reactor in four approximately equal aliquots that maintained the reaction temperature at −8° C. to −7° C. The total addition time for the triethylamine was 5 minutes. After addition of the first aliquot of triethylamine, the light amber colored, transparent solution transformed to a light yellow colored hazy solution indicative of triethylamine hydrobromide production.

After 30 minutes of postreaction at −6° C. to −4.5° C., the product solution was added to a beaker of magnetically stirred deionized water (1 liter) and dichloromethane (500 milliliters). After 2 minutes of stirring, the mixture was added to a separatory funnel, allowed to settle, and then the dichloromethane layer recovered, with the aqueous layer discarded to waste. The dichloromethane solution was added back into the separatory funnel and extracted with fresh deionized water (125 milliliters). The resultant hazy dichloromethane solution was dried over granular anhydrous sodium sulfate to give a clear solution that was then passed through a bed of anhydrous sodium sulfate supported on a 400 milliliter, medium fritted glass funnel attached to a side arm vacuum flask. The clear, light yellow colored filtrate was rotary evaporated using a maximum oil bath temperature of 50° C. until a vacuum of 0.25 mm Hg was achieved. The solid product was then placed in the vacuum oven at 75° C. and dried for 16 hours. A total of 2.06 grams of solid, golden yellow colored product was recovered. FTIR analysis of a potassium bromide pellet of the polycyanate of the polyphenol of cyclododecane trialdehyde revealed the presence of a minor amount of hydroxyl group absorbance at 3422.7 $cm^{-1}$ concurrent with the appearance of strong cyanate group absorbance at 2264.5, 2235.2 and 2208.8 $cm^{-1}$. After removing the hydroxyl group absorbance contributed by trace water in the KBr powder used to form the KBr pellet, the intensity ratio of hydroxyl group absorbance (3422.7 $cm^{-1}$) to aromatic ring absorbance at 1499.1 $cm^{-1}$ was 0.26. The intensity ratio of cyanate group absorbance (2264.5 $cm^{-1}$) to aromatic ring absorbance (1499.1 $cm^{-1}$) was 1.13. HPLC analysis revealed the polycyanate of the polyphenol of cyclododecane trialdehyde included multiple components eluting between 5.74 to 11.02 min, with 2 predominant components comprising 27.5 and 24.3 area % (phenyl cyanate residual comprising 1.18 area % eluted at 3.53 min). Each component present had a different retention time than those observed in the HPLC analysis of the polyphenol of cyclododecane trialdehyde reactant.

Example 2

Synthesis of the Homopolytriazine of Polycyanate of the Polyphenol of Cyclododecane Trialdehyde (Containing Residual Unreacted Hydroxyl)

Differential scanning calorimetry (DSC) analysis of a portion (8.6 milligrams) of polycyanate of the polyphenol of cyclododecane trialdehyde from Example 1 was completed using a rate of heating of 7° C. per minute from 25° C. to 400° C. under a stream of nitrogen flowing at 35 cubic centimeters per minute. A DSC 2910 Modulated DSC (TA Instruments) was used for the analysis. No melt endotherm was detected. A sharp exotherm attributed to cyclotrimerization was detected with a 120.3° C. onset, a 212.3° C. midpoint, and a 247.4° C. end accompanied by an enthalpy of 166.7 joules per gram. This was followed by a second broad exotherm with a 253.5° C. onset, a 324.5° C. midpoint, and a 380.5° C. end accompanied by an enthalpy of 59.2 joules per gram.

Example 3

Preparation of a Clear Unfilled Casting of the Homopolytriazine of Polycyanate of the Polyphenol of Cyclododecane Trialdehyde (Containing Residual Unreacted Hydroxyl)

Polycyanate of the polyphenol of cyclododecane trialdehyde (0.5 gram) from Example 1 was added to an aluminum dish and placed into an oven preheated to 100° C. After 1 hour, the dish containing solid polycyanate was transferred to a 150° C. oven and held therein for one hour. The product was then held a 200° C. for one hour followed by slow cooling to room temperature (22° C.). The homopolytriazine product was a transparent, amber colored, rigid solid. DSC analysis of a portion (23.2 milligrams) of the product was completed using the method of Example 2 with a rate of heating of 7° C. per minute from 0° C. to 375° C. under a stream of nitrogen flowing at 35 cubic centimeters per minute. A broad exotherm was detected with a 218.9° C. onset, a 292.7° C. midpoint, and a 372.0° C. end accompanied by an enthalpy of 79.3 joules per gram. A second scanning DSC analysis revealed a weak glass transition temperature of 297.1° C. The homopolytriazine recovered from the DSC analysis was a transparent, amber colored, rigid solid.

Comparative Example 1

Synthesis of the Homopolytriazine of Bisphenol A Dicyanate

DSC analysis of bisphenol A dicyanate (10.1 milligrams) was completed using a rate of heating of 7° C. per minute from 25° C. to 350° C. under a stream of nitrogen flowing at 35 cubic centimeters per minute. The bisphenol A dicyanate used was free of unreacted hydroxyl. A single sharp melt endotherm attributable to melting was detected with an 83.0° C. midpoint accompanied by an enthalpy of 98.7 joules per gram. A single exotherm attributed to cyclotrimerization was detected with a 244.1° C. onset, a 320.7° C. midpoint, and a 352.6° C. end accompanied by an enthalpy of 588.9 joules per gram. A second scanning of the resultant homopolytriazine revealed minor further exothermicity commencing at 319.9° C. (note: there was a gradual exothermic shift starting at 150° C.). A third scanning revealed exothermicity commencing at 209.8° C. with a more pronounced exothermic shift commencing at 320.4° C. The homopolytriazine recovered from the DSC analysis was a transparent, light amber colored, rigid solid.

Comparative Example 2

Preparation of a Clear Unfilled Casting of the Homopolytriazine of Bisphenol A Dicyanate The method of Example 3 was repeated using bisphenol A dicyanate (0.5 gram, same as used in Comparative Example 1), with additional curing in the oven at 250° C. for one hour and 300° C. for one hour. It was noted that the bisphenol A dicyanate became a homogeneous liquid while in the oven at 100° C. The homopolytriazine product was a transparent, yellow colored, rigid solid. DSC analysis of a portion (19.5 milligrams) of the product using the method of Comparative Example 1 revealed a strong glass transition with a temperature of 275.7° C.

Example 4

Preparation of Polycyanate of Polyphenol of Cyclododecane Trialdehyde (Free of Residual Unreacted Hydroxyl)

The method of Example 1 was repeated using the following reactants, solvent, and stoichiometry: 2.56 grams of polyphenol of cyclododecane trialdehyde (nominally 0.02 hydroxyl equivalent) from Reference Example 1, anhydrous acetone (75 milliliters), cyanogen bromide (2.65 grams, 0.025 mole, 1.25:1 cyanogen bromide:nominal hydroxyl equivalent ratio) and triethylamine (2.53 grams, 0.025 mole, 1.25 triethylamine:nominal hydroxyl equivalent ratio). The triethylamine was added to the reactor in eight approximately equal aliquots that maintained the reaction temperature at −8° C. to −5° C. The total addition time for the triethylamine was 17 minutes. After addition of the third aliquot of triethylamine, the light amber colored, transparent solution transformed to a golden yellow colored slurry indicative of triethylamine hydrobromide production.

After 40 minutes of postreaction at −7° C. to −4.5° C., the product slurry was filtered through a medium fritted glass funnel into a flask containing magnetically stirred deionized water (800 milliliter). After 1 minutes of stirring, the fine slurry was added to a separatory funnel, and extracted with four portions (500 milliliters) of dichloromethane. The combined dichloromethane extract was dried over granular anhydrous sodium sulfate and the slurry filtered through paper (Whatman 114V) supported in a funnel. The clear, light yellow colored filtrate was rotary evaporated and dried using the method of Example 1B. A total of 2.28 grams of solid, golden yellow colored product was recovered. FTIR analysis of a potassium bromide pellet of the polycyanate of the polyphenol of cyclododecane trialdehyde revealed disappearance of the hydroxyl group absorbance at 3382.3 $cm^{-1}$ concurrent with the appearance of strong cyanate group absorbance at 2264.1, 2235.4 and 2208.7 $cm^{-1}$. The intensity ratio of cyanate group absorbance (2264.1 $cm^{-1}$) to aromatic ring absorbance (1498.8 $cm^{-1}$) was 1.14. HPLC analysis revealed the polycyanate of the polyphenol of cyclododecane trialdehyde included multiple components eluting between 5.88 to 11.02 min, with 2 predominant components comprising 34.2 and 23.8 area % (phenyl cyanate residual comprising 0.76 area % eluted at 3.52 min). Each component present had a different retention time than those observed in the HPLC analysis of the polyphenol of cyclododecane trialdehyde reactant.

Example 5

Synthesis of the Homopolytriazine of Polycyanate of the Polyphenol of Cyclododecane Trialdehyde (Free of Residual Unreacted Hydroxyl)

DSC analysis of a portion (8.3 milligrams) of polycyanate of the polyphenol of cyclododecane trialdehyde from Example 4 was completed using the method of Example 2.

No melt endotherm was detected. A sharp exotherm attributed to cyclotrimerization was detected with a 150.2° C. onset, a 229.3° C. midpoint, and a 264.4° C. end accompanied by an enthalpy of 142.3 joules per gram. This was followed by a second broad exotherm with a 272.0° C. onset, a 324.6° C. midpoint, and a 375.3° C. end accompanied by an enthalpy of 38.6 joules per gram.

Example 6

Preparation of a Clear Unfilled Casting of the Homopolytriazine of Polycyanate of the Polyphenol of Cyclododecane Trialdehyde (Free of Residual Unreacted Hydroxyl)

Polycyanate of the polyphenol of cyclododecane trialdehyde (0.5 gram) from Example 4 was added to an aluminum dish and cured using the method of Example 3. The homopolytriazine product was a transparent, amber colored, rigid solid. DSC analysis of a portion (21.2 milligrams) of the product was completed using the method of Example 2 (heating of 7° C. per minute from 25° C. to 400° C.). A broad exotherm was detected with a 216.6° C. onset, a 310.1° C. midpoint, and a 386.2° C. end accompanied by an enthalpy of 101.7 joules per gram. Second, third and fourth scanning DSC analyses did not detect a glass transition temperature, but did reveal an exothermic shift at 344.5° C. in the second scan (no exothermicity present in the third and fourth scans). The homopolytriazine recovered from the DSC analysis was a transparent, amber colored, rigid solid.

Example 7

Copolymerization of Polycyanate of Polyphenol of Cyclododecane Trialdehyde and Bisphenol A Dicyanate Polycyanate of the polyphenol of cyclododecane trialdehyde (0.1100 gram) from Example 4 and bisphenol A dicyanate (same as that used in Comparative Examples 1 and 2) (0.1100 gram) were weighed into a glass vial using a scale with four place accuracy. Dichloromethane (1 milliliter) was added to the vial which was then sealed and shaken to provide a solution. The solution was poured into an aluminum dish and the bulk of the dichloromethane was evaporated off in a vented hood. The solid product in the aluminum dish was then placed in a vacuum oven and dried at 22° C. for 1 hour. The solid blend was a hard, crystalline powder which could be ground to a non-sintering (at room temperature) powder.

DSC analysis of a portion of the blend (10.8 milligrams) was completed using a rate of heating of 7° C. per minute from 25° C. to 400° C. under a stream of nitrogen flowing at 35 cubic centimeters per minute. A single sharp melt endotherm attributable to melting was detected with a 65.5° C. midpoint accompanied by an enthalpy of 20.6 joules per gram. A single exotherm attributed to cocyclotrimerization was detected with a 165.4° C. onset, a 248.8° C. midpoint, and a 336.9° C. end accompanied by an enthalpy of 339.2 joules per gram. A second scanning of the resultant copolytriazine revealed very minor further exothermicity commencing at 379.1° C. The copolytriazine recovered from the DSC analysis was a transparent, light amber colored, rigid solid.

Example 8

Preparation of a Clear Unfilled Casting of the Copolytriazine of Polycyanate of Polyphenol of Cyclododecane Trialdehyde and Bisphenol A Dicyanate The method of Example 3 was repeated using the remaining blend of polycyanate of the polyphenol of cyclododecane trialdehyde and bisphenol A dicyanate from Example 7, with additional curing in the oven at 250° C. for one hour and 300° C. for one hour. The copolytriazine product was a transparent, amber colored, rigid solid. DSC analysis of a portion (23.4 milligrams) of the product was completed using the method of Example 2 (heating of 7° C. per minute from 0° C. to 360° C.). A broad, flat exotherm was detected with a 308.0° C. onset, a 340.6° C. midpoint, and a 357.2° C. end accompanied by an enthalpy of 2.6 joules per gram. A second scanning (heating of 7° C. per minute from 0° C. to 370° C.) revealed a glass transition temperature of 340.3° C. The copolytriazine recovered from the DSC analysis was a transparent, amber colored, rigid solid.

Example 9

Copolymerization of Polycyanate of Polyphenol of Cyclododecane Trialdehyde and Bismaleimide of 4,4'-Diaminodiphenylmethane Polycyanate of the polyphenol of cyclododecane trialdehyde (0.1105 gram) from Example 4 and bismaleimide of 4,4'-diaminodiphenylmethane (0.1105 gram) were weighed into a glass vial using a scale with four place accuracy. Dichloromethane (1 milliliter) was added to the vial which was then sealed and shaken to provide a solution. The solution was poured into an aluminum dish and the bulk of the dichloromethane was evaporated off in a vented hood. The solid product in the aluminum dish was then placed in a vacuum oven and dried at 22° C. for 1 hour.

DSC analysis of a portion of the blend (11.0 milligrams) was completed using a rate of heating of 7° C. per minute from 25° C. to 400° C. under a stream of nitrogen flowing at 35 cubic centimeters per minute. A single sharp melt endotherm attributable to melting was detected with a 144.3° C. midpoint accompanied by an enthalpy of 23.9 joules per gram. A single exotherm attributed to copolymerization was detected with a 154.5° C. onset, a 227.5° C. midpoint, and a 364.9° C. end accompanied by an enthalpy of 236.5 joules per gram. The copolymer recovered from the DSC analysis was a transparent, amber colored, rigid solid.

Example 10

Preparation of a Clear Unfilled Casting of the Copolymer of Polycyanate of Polyphenol of Cyclododecane Trialdehyde and Bismaleimide of 4,4'-Diaminodiphenylmethane The method of Example 3 was repeated using the remaining blend of polycyanate of the polyphenol of cyclododecane trialdehyde and bismaleimide of 4,4'-diaminodiphenylmethane from Example 9, with additional curing in the oven at 250° C. for one hour and 300° C. for one hour. The copolymer product was a transparent, amber colored, rigid solid. DSC analysis of a portion (18.1 milligrams) of the product was completed using the method of Example 2 (heating of 7° C. per minute from 0° C. to 400° C.). A broad, flat exotherm was detected with a 309.5° C. onset, a 335.9° C. midpoint, and a 361.1° C. end accompanied by an enthalpy of 1.5 joules per gram, immediately followed by an exothermic upshift at 374.4° C. A second scanning (heating of 7° C. per minute from 0° C. to 400° C.) did not detect a glass transition temperature. The copolymer recovered from the DSC analysis was a transparent, amber colored, rigid solid.

| Example | Cure Onset (° C.) | Cure Midpoint (° C.) | Cure End (° C.) | Enthalpy (joules per gram) | Tg (° C.) |
|---|---|---|---|---|---|
| Examples 5 and 6 | 150.2 | 229.3 | 264.4 | 142.3 | >400 |
|  | 272.0 | 324.6 | 375.3 | 38.6 |  |
| Examples 7 and 8 | 165.4 | 248.8 | 336.9 | 339.2 | 340.3 |
| Examples 9 and 10 | 154.5 | 227.5 | 364.9 | 236.5 | >400 |
| Comparative Examples 1 and 2 | 244.1 | 320.7 | 352.6 | 588.9 | 275.7 |

What is claimed is:

1. Polycyanates of the formula:

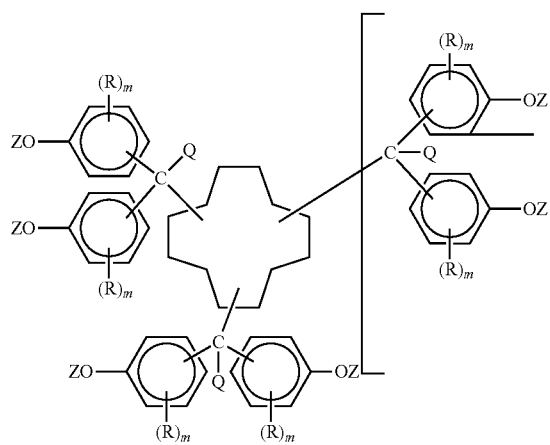

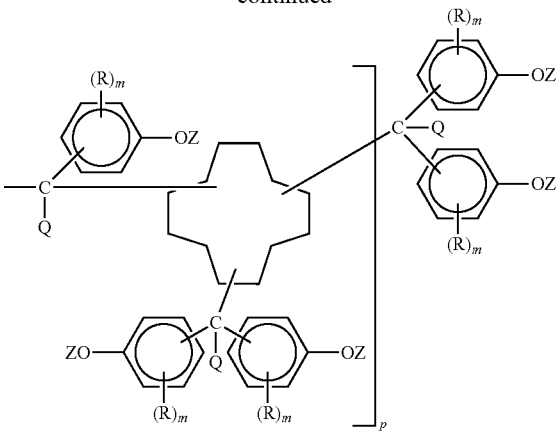

where
each m independently has a value of zero to 3;
p has a value of one to 20;
each R is independently halogen; nitrile; nitro; $C_1$-$C_6$ alkyl or $C_1$-$C_6$ alkoxy; wherein the alkyl and alkoxy groups may be substituted with one or more halogen atoms, $C_2$-$C_6$ alkenyl, or $C_2$-$C_6$ alkenyloxy;
each Z is H or —C≡N, wherein at least 25% of the Z groups are —C≡N; and
each Q is independently hydrogen or $C_1$-$C_6$ alkyl,
or when m is 2, two R groups may independently be a $C_3$-$C_4$ alkylene group that optionally contains one or two double bonds and is bonded to two adjacent carbons on the ring to which they are attached; thereby producing a fused, bicyclic ring.

2. Polycyanates of claim 1, wherein R is H.

3. Polycyanates of claim 1, wherein Q is H or $C_1$-$C_2$ alkyl.

4. Polycyanates of claim 1, wherein at least 50% of the Z groups are —C≡N.

5. Polycyanates of claim 1, wherein p is 0 or 1.

6. Polycyanates of claim 1, wherein 80-100% of the Z groups are —C≡N.

7. Methods of making the compounds of claim 1, comprising reacting polyphenols of the formula:

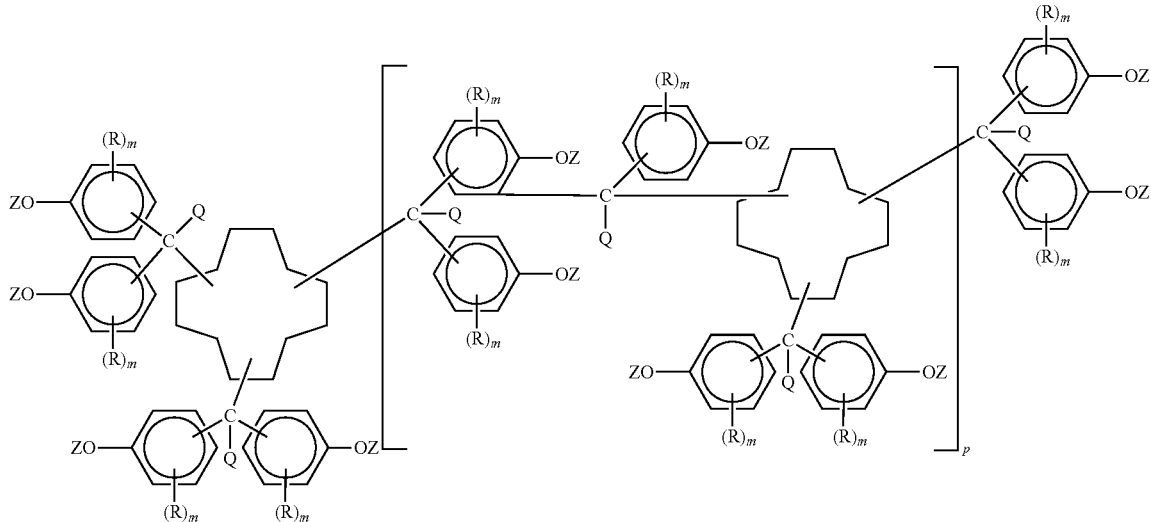

where
each m independently has a value of zero to 3;
p has a value of 1 to 20;
each R is independently halogen; nitrile; nitro; $C_1$-$C_6$ alkyl or $C_1$-$C_6$ alkoxy;
wherein the alkyl and alkoxy groups may be substituted with one or more halogen atoms, $C_2$-$C_6$ alkenyl, or $C_2$-$C_6$ alkenyloxy;
each Z is H or —C≡N, wherein at least 25% of the Z groups are —C≡N; and
each Q is independently hydrogen or $C_1$-$C_6$ alkyl,
or when m is 2, two R groups may independently be a $C_3$-$C_4$ alkylene group that optionally contains one or two double bonds and is bonded to two adjacent carbons on the ring to which they are attached; thereby producing a fused, bicyclic ring;
with a cyanogen halide in the presence of a base, and optionally in the presence of a catalyst, a solvent or both.

8. Methods of claim 7, wherein the reaction is conducted in the presence of at least one solvent.

9. Methods of claim 7, wherein at least one solvent is an aliphatic ketone, cycloaliphatic ketone, chlorinated hydrocarbon or a mixture thereof.

10. Methods of claim 7, wherein the base is a tertiary amine.

11. Methods of claim 7, wherein the cyanogen halide is cyanogen chloride or cyanogen bromide.

12. Methods of claim 7, wherein the reaction temperature is −10° C. to 0° C.

13. Curable compositions comprising a polycyanate of the formula:

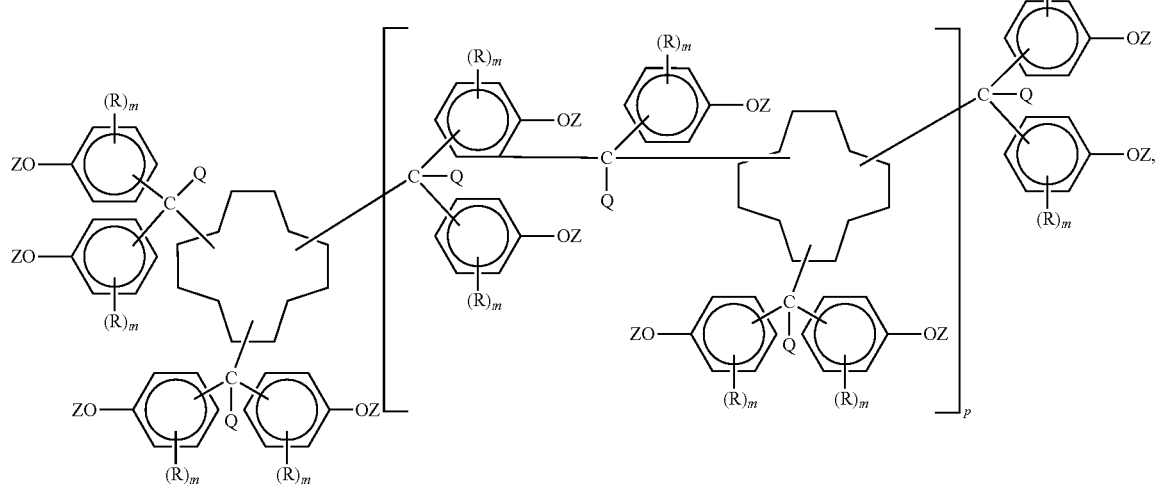

where
each m independently has a value of zero to 3;
p has a value of 1 to 20;
each R is independently halogen; nitrile; nitro; $C_1$-$C_6$ alkyl or $C_1$-$C_6$ alkoxy; wherein the alkyl and alkoxy groups may be substituted with one or more halogen atoms, $C_2$-$C_6$ alkenyl, or $C_2$-$C_6$ alkenyloxy;
each Z is H or —C≡N, wherein at least 25% of the Z groups are —C≡N; and
each Q is independently hydrogen or $C_1$-$C_6$ alkyl,
or when m is 2, two R groups may independently be a $C_3$-$C_4$ alkylene group that optionally contains one or two double bonds and is bonded to two adjacent carbons on the ring to which they are attached; thereby producing a fused, bicyclic ring; and,
optionally at least one curing catalyst and/or curing accelerator.

14. Curable compositions of claim 13, further comprising one or more thermosettable monomers other than the polycyanate of claim 1.

15. Curable compositions of claim 14, wherein the thermosettable monomer further comprises one or more of 1) di- or poly(cyanate) other than the cyanate of claim 1, 2) bis- or poly(maleimide), 3) epoxy resin, 4) di- or poly(isocyanate), 5) di or poly(cyanamide), or 6) polymerizable mono-, di-, or poly(ethylenically unsaturated) monomers.

16. Curable compositions of claim 15 further comprising optionally at least one curing catalyst and/or curing accelerator.

17. Partially oligomerized or polymerized (B-staged) products, or cured (thermoset) products prepared from the curable compositions of claim 16.

18. Cured compositions prepared from the curable compositions of claim 17 that are structural or electrical laminate and/or composites, multilayer electronic circuitry, integrated circuit packaging (such as "IC substrates"), filament windings, moldings, encapsulations, castings, composites for aerospace applications, adhesives, functional powder coatings and other protective coatings.

19. Cured compositions of claim 18 in the form of sheets, films, fibers or other shaped articles.

* * * * *